US012667423B2

(12) United States Patent
Lastarria

(10) Patent No.: US 12,667,423 B2
(45) Date of Patent: Jun. 30, 2026

(54) LASER ABLATION SURGERY SYSTEM WITH SAFETY CONTROL OF TEMPERATURE AND PRESSURE AT SURGICAL SITE AND METHOD OF USE

(71) Applicant: Emilio Lastarria, Miami, FL (US)

(72) Inventor: Emilio Lastarria, Miami, FL (US)

(73) Assignee: EMILIO Lastarria, Miami, FL (US)

( * ) Notice: Subject to any disclaimer, the term of this patent is extended or adjusted under 35 U.S.C. 154(b) by 301 days.

(21) Appl. No.: 18/689,793

(22) PCT Filed: Sep. 7, 2022

(86) PCT No.: PCT/US2022/076011
§ 371 (c)(1),
(2) Date: Mar. 6, 2024

(87) PCT Pub. No.: WO2023/039394
PCT Pub. Date: Mar. 16, 2023

(65) Prior Publication Data
US 2024/0366304 A1 Nov. 7, 2024

Related U.S. Application Data

(60) Provisional application No. 63/241,591, filed on Sep. 8, 2021.

(51) Int. Cl.
*A61B 18/26* (2006.01)
*A61B 18/00* (2006.01)
(Continued)

(52) U.S. Cl.
CPC .............. *A61B 18/26* (2013.01); *A61B 90/06* (2016.02); *G16H 50/30* (2018.01);
(Continued)

(58) Field of Classification Search
CPC .................... A61B 18/26; A61B 90/06; A61B 2018/00511; A61B 2018/00517;
(Continued)

(56) References Cited

U.S. PATENT DOCUMENTS 6,618,620 B1 9/2003 Freundlich
9,403,029 B2 * 8/2016 Gowda ................ A61N 5/0601
(Continued)

FOREIGN PATENT DOCUMENTS

DE 202017102316 5/2017

OTHER PUBLICATIONS

International Search Report & Written Opinion, PCT/US 22/76011 dated Dec. 14, 2022, Authorized Officer Kari Rodriguez.

*Primary Examiner* — Jonathan T Kuo
(74) *Attorney, Agent, or Firm* — Fleit Intellectual Property Law; Jose Gutman

(57) ABSTRACT

A laser ablation surgery system (10) with safety control of temperature and pressure at a surgical site. The system includes a laser source (20) that produces through a laser fiber a laser beam at a wavelength absorbable by an ablation target. An endoscope (40) has at least one lumen configured to feed an irrigation fluid (4) therethrough to the surgical site. At least one temperature sensor (80) and at least one pressure sensor (140) are disposed at a distal end of the endoscope. The sensors are configured to monitor temperature of the irrigation fluid, and fluid pressure, at the surgical site. A system control (100) includes a patient injury risk calculator (102) configured to perform a preoperative injury risk assessment, and in real time an intraoperative thermal injury assessment and fluid pressure injury assessment based on the fluid temperature and pressure detected by the sensors at the surgical site.

18 Claims, 5 Drawing Sheets

(51) Int. Cl.
　　*A61B 90/00*　　　(2016.01)
　　*G16H 50/30*　　　(2018.01)
(52) U.S. Cl.
　　CPC .............. *A61B 2018/00511* (2013.01); *A61B 2018/00517* (2013.01); *A61B 2018/00577* (2013.01); *A61B 2018/00648* (2013.01); *A61B 2018/00672* (2013.01); *A61B 2018/00678* (2013.01); *A61B 2018/00708* (2013.01); *A61B 2018/00744* (2013.01); *A61B 2018/00791* (2013.01); *A61B 2018/00863* (2013.01); *A61B 2018/00982* (2013.01); *A61B 2090/064* (2016.02); *A61B 2218/002* (2013.01)
(58) Field of Classification Search
　　CPC ........... A61B 2018/00577; A61B 2018/00648; A61B 2018/00672; A61B 2018/00678; A61B 2018/00708; A61B 2018/00744; A61B 2018/00791; A61B 2018/00863; A61B 2018/00982; A61B 2090/064; A61B 2218/002; A61B 2017/00123; A61B 2018/00035; A61B 2018/00166; A61B 2018/0066; A61B 2018/00702; A61B 2018/00714; A61B 2018/00726; A61B 2018/00732; A61B 2018/00761; A61B 2018/00815; A61B 2018/00821; A61B 2018/00589; A61B 2018/00595; A61B 2018/00898; A61B 18/20–18/28; G16H 50/30
　　See application file for complete search history.

(56) References Cited

U.S. PATENT DOCUMENTS

| | | | |
|---|---|---|---|
| 9,956,040 B1 * | 5/2018 | Lastarria | A61B 18/22 |
| 2009/0198309 A1 * | 8/2009 | Gowda | A61N 5/0601 |
| | | | 607/102 |
| 2017/0333614 A1 | 11/2017 | Gao et al. | |
| 2018/0055568 A1 | 3/2018 | Shelton et al. | |

* cited by examiner

LASER ABLATION SURGERY SYSTEM WITH SAFETY CONTROL OF TEMPERATURE AND PRESSURE AT SURGICAL SITE AND METHOD OF USE

CROSS-REFERENCE TO RELATED APPLICATIONS

This application claims priority from and is related to the following prior application Patent Cooperation Treaty Patent PCT/US2022/076011, filed on 7 Sep. 2022, which claims priority to U.S. Provisional Patent Application No. 63/241,591, filed on 8 Sep. 2021. These prior applications, including the entirety of their written description and drawings, are collectively hereby incorporated by reference into the present application.

BACKGROUND

The present disclosure generally relates to a laser surgery system, and more specifically relates to a laser ablation surgery system with safety control of the temperature at a surgical site of a laser ablation surgery and method of use.

Intracorporeal laser lithotripsy is the most performed endourological procedure by urologists for treating ureteral and kidney stones as well as bladder and urethral stones. Endoscopic approach is the gold standard and retrograde ureteral and intra-renal ureteroscopy are the most common procedures performed for kidney and ureteral stones treatment.

During a laser lithotripsy for treating upper urinary tract calculi, a surgeon inserts a laser fiber endoscopically to be in direct contact with a kidney or ureteral stone and then actives a laser system to deliver laser pulses to fragment the stone. Various laser techniques have been developed for effectively breaking a stone to small pieces which can be extracted with a basket endoscopically or to fine debris which can be passed and cleared out of the urinary system. The laser lithotripsy procedure is normally performed with fluid irrigation. An irrigation fluid is provided to the surgical site, where the stone is laser ablated, through a working channel of an ureteroscope for treating upper urinary tract calculi or through a flow sheath of a cystoscope for treating lower urinary tract calculi. The irrigation fluid maintains a clear field of vision and cools the laser fiber and surrounding tissue for preventing thermal injury of the surrounding tissues during laser ablation.

Holmium:yttrium-aluminum-garnet (Ho:YAG) laser is widely used for lithotripsy. It is a highly efficient platform available for fragmenting all kidney and ureteral stone compositions. However, high power laser emission for efficient stone ablation increases temperature at the surgical site. It was reported in an in-vitro study that temperatures can reach 60° C. after only 10 seconds of laser activation at 40 W. Studies have shown temperatures above 43° C. represent an increased risk for tissue damage. Increments in intra-renal temperature can lead to irreversible cellular damage by protein denaturation, in addition to cell's genetic expression and composition damages, evolving to urothelial cellular death. Therefore, a major concern for laser litho-tripsy is potential thermal effects on surrounding urothelium and renal tissue.

A new thulium fiber laser (TFL) for lithotripsy, which is a silica core doped by active thulium ions and pumped by diode laser, recently developed with unique features. The new thulium fiber laser can use pulse energy as low as 0.025 J, extremely high frequencies (up to 2000 Hz) and a thin silica fiber as small as 50 μm, which has a feature of low pulse energy yet a high energy density. These properties enabled faster lithotripsy compared to the Ho:YAG systems with less stone retropulsion. However, it was reported recently that a higher temperature increase with the TFL laser in comparison to the Ho:YAG laser and an even greater rise when using higher frequencies were observed in vitro.

Known postoperative clinical complications associated with thermal injuries may include urothelial lesions, stricture of ureter, peri-renal collections, osteitis pubis, bladder mucosal scald burn, etc. In the case of ureteral stricture, it is often silent in early postoperative symptoms and it can lead to severe complications. Loss of renal function due to ureteral stricture has been reported.

However, technology for safe operation of surgical laser in urology is lacking. Currently, no laser surgical system monitors or controls the temperature at the surgical site during the laser lithotripsy surgery, and existing laser systems operate independently from irrigation management. In the absence of actual measurement of the temperature at the surgical site during the laser lithotripsy surgery, the temperature at the surgical site is controlled blindly by surgeons based on their experiences and observations. Surgeons take frequent breaks during laser ablation of the stone and allow the irrigation fluid to cool down the surgical site. Lack of actual knowledge of the temperature at surgical site during the surgery presents a significant risk to patient safety, because even a short time exposure to elevated temperatures could cause thermal injury to the surrounding tissue and result in postoperative complications.

The laser lithotripsy procedure requires uninterrupted fluid irrigation. However, currently, the irrigation during laser lithotripsy is usually provided manually. A sterile saline solution at room temperature is used as the irrigation fluid, which is contained in a flexible bag and connected to an ureteroscope or cystoscope through a tubing. The irrigation fluid is delivered by gravity feeding with pressure, using the flexible saline bag wrapped in a pressurized cuff and suspended on an IV pole. The flow rate is controlled manually with a regulating clamp by the operating room staff. During a surgery, the supply of the irrigation fluid is visually monitored by the supporting staff, and the saline bag may need to be timely replaced when the fluid runs low or runs out. Therefore, the risk of thermal injury during laser litho-tripsy is further escalated by current practice of manual control of fluid irrigation due to potential human errors or mechanical failures in managing the irrigation fluid. The risk of injury to the patient can include both risk of thermal injury at a surgical site and risk of fluid pressure injury at the surgical site.

Therefore, there is a strong need for an improved laser ablation surgical system and safety measures that are able to monitor the temperature at the surgical site and the irrigation condition during a laser lithotripsy for treating urinary tract calculi so that the temperature at the surgical site can be effectively controlled to ensure patient safety and reduce postoperative complications.

BRIEF SUMMARY

According to various embodiments, a laser ablation surgery system provides safety control of surgical site temperature. The system includes: a laser source configured to produce a laser beam at a wavelength absorbable by an ablation target through a laser fiber connected thereto; an endoscope having one or more lumens with at least one lumen configured to feed an irrigation fluid therethrough and having at least one temperature sensor disposed at a distal end of the endoscope, the temperature sensor being configured to monitor a temperature of the irrigation fluid at a surgical site of a laser ablation surgery in real time; and a system control operably connected to the at least one temperature sensor, the system control comprising a patient injury risk calculator configured to perform a real time thermal injury assessment utilizing the temperature of the irrigation fluid at the surgical site detected by the at least one temperature sensor during the laser ablation surgery.

According to various embodiments, the endoscope has at least one fluid pressure sensor disposed at the distal end of the endoscope. The fluid pressure sensor is configured to monitor a fluid pressure of the irrigation fluid at the surgical site of the laser ablation surgery in real time. The system control is operably connected to the at least one fluid pressure sensor. The patient injury risk calculator is configured to perform a real time fluid pressure injury assessment utilizing the fluid pressure of the irrigation fluid at the surgical site detected by the at least one fluid pressure sensor during the laser ablation surgery.

Features and advantages of the various embodiments will become readily apparent from the following description and accompanying drawings. Certain preferred embodiments of the invention and their benefits will also become more apparent to a person of ordinary skill in the art through the description and selected examples given herein below, and through the appended claims.

All references, publications, patents, and patent applications, cited herein and/or cited in any accompanying Information Disclosure Statement (IDS), are hereby incorporated herein by reference in their entirety for all purposes.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

Figure 1:
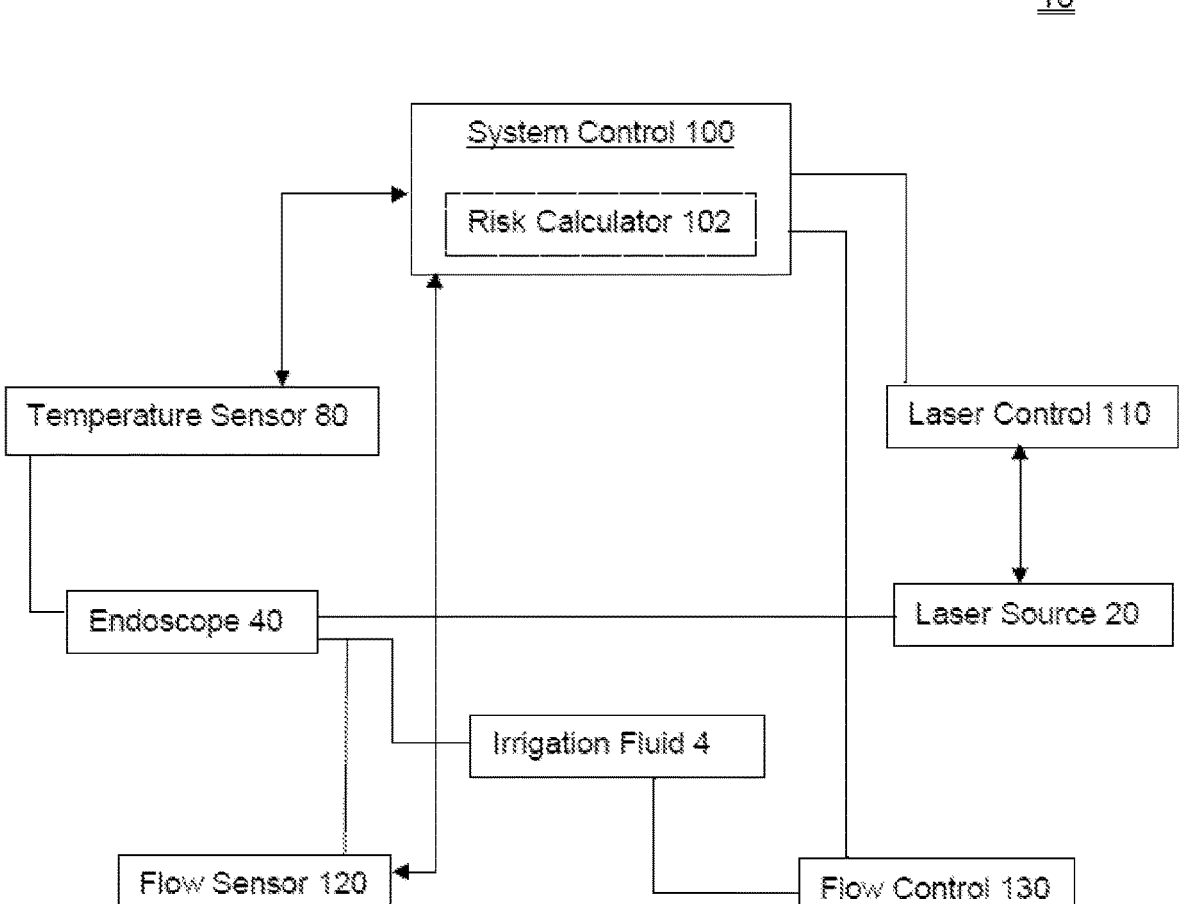
FIG. 1 is a schematic block diagram of the laser ablation surgery system in one embodiment of the present invention.

As required, detailed embodiments are disclosed herein; however, it is to be understood that the disclosed embodiments are merely examples and that the devices, systems and methods described herein can be embodied in various forms.

Therefore, specific structural and functional details disclosed herein are not to be interpreted as limiting, but merely as a basis for the claims and as a representative basis for teaching one of ordinary skill in the art to variously employ the disclosed subject matter in virtually any proprietary detailed structure and function. Further, the terms and phrases used herein are not intended to be limiting, but rather, to provide an understandable description. Additionally, unless otherwise specifically expressed or clearly understood from the context of use, a term as used herein describes the singular and/or the plural of that term.

The terms "a" or "an", as used herein, are defined as one or more than one. The term "plurality", as used herein, is defined as two or more than two. The term "another", as used herein, is defined as at least a second or more. The terms "including" and "having," as used herein, are defined as comprising i.e., open language. The term "coupled," as used herein, is defined as "connected," although not necessarily directly, and not necessarily mechanically.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

In some embodiments, a laser ablation surgery system 10 includes safety control of temperature at a surgical site of a laser ablation surgery. The system, according to these embodiments, utilizes real time monitoring of the detected temperature of an irrigation fluid at the surgical site. The system, according to various embodiments, can monitor in real time the detected pressure of the irrigation fluid at the surgical site. In some example embodiments, the laser ablation surgery system is structured for retrograde ureteroscopic laser lithotripsy for treating urinary tract calculi. In such laser lithotripsy surgeries, the ablation target is one or more stones in the kidney, ureter, bladder, or urethra of a patient.

Herein, the term of ablation target refers to the subject of laser ablation, and the term of surgical site refers to the location where the ablation target is subject to laser ablation. The surgical site in various embodiments is located inside of a patient being treated with laser ablation surgery.

In a laser ablation surgery, the soft tissue located at the surgical site, which is not the ablation target, i.e., non-target soft tissue, is a concern of potential thermal injury due to exposure to an elevated temperature at the surgical site during a laser ablation surgery. In a laser ablation surgery, the soft tissue located at the surgical site, or in the vicinity thereof, which is not the ablation target, i.e., non-target soft tissue, can also be a concern of potential fluid pressure injury due to exposure to an elevated fluid pressure at the surgical site during a laser ablation surgery. In an example embodiment of ureteroscopic laser lithotripsy, the surgical site is where a stone is located in the kidney, ureter, bladder or urethra of a patient, and more specifically where the stone is laser ablated during laser lithotripsy. In laser lithotripsy for treating urinary tract stones, the soft tissue of concern is the soft tissue surrounding or in the vicinity of the stone where the laser ablation occurs, such as renal pelvis, renal calyces, ureter, bladder or urethra, or the like. Such soft tissue may be exposed to an elevated temperature during laser ablation and subject to a potential thermal injury in a surgery. Such soft tissue may be exposed to an elevated fluid pressure during laser ablation and subject to a potential fluid pressure injury in a surgery.

It should be understood that in one laser lithotripsy procedure, more than one surgical site may be involved. During an ureteroscopic laser lithotripsy surgery, for example, a large stone is initially fragmented to smaller pieces. The smaller pieces may bounce around the original location and strike surrounding surface, or may migrate to different locations due to stone retropulsion after laser impact. To further treat the smaller pieces, until being broken down sufficiently to sizes which can be extracted by basketing or reduced to dust which can pass freely on their own, the distal end of the ureteroscope may need to be repositioned to the migrated locations. Thus, the surgical site herein refers to each location where laser ablation occurs. As can be appreciated, according to this example, during laser lithotripsy for treating urinary tract stones, several elements are present at a surgical site, which include the ablation target, i.e., stone, soft tissue surrounding or in the vicinity of the stone, the distal end of the ureteroscope placed directly against or adjacent the stone, and irrigation fluid typically surrounding the stone and the distal end of the ureteroscope.

In one embodiment as shown in FIG. 1, the laser ablation surgery system 10 comprises a laser source 20, an endoscope 40 having at least one temperature sensor 80 disposed at a distal end of the endoscope 40, and a system control 100.

The laser source 20 is configured to produce a laser beam through a laser fiber 90 (see FIG. 3) connected thereto and is operably connected to system control 100. The laser beam emitted from the tip 92 of the laser fiber 90 is at a wavelength absorbable by the ablation target (e.g., a stone) that is subjected to laser ablation. A majority of urinary tract calculi or stones are made of minerals in the urine that form crystals. Nearly 80% of the stones are composed of calcium, and the remainder is composed of various substances, including uric acid, cystine or struvite. Dense stones such as calcium oxalate monohydrate, brushite (calcium phosphate), cystine calculus have greater hardness and fracture toughness. Stone contains small pockets of water within its crystalline structure. Under laser radiation, the laser energy is absorbed by the water and rapid expanding pressure from micro-explosive vaporization fragments the stone. See, for example, the stone 2 shown in FIGS. 5 and 6. Both holmium and thulium lasers are absorbable by water. Ureteroscopic laser lithotripsy can treat stone size up to 20 mm. Calculus near-infrared wavelength material absorption can also be used to optimize wavelength selection for the treatment, for example, calculus oxalate monohydrate has more material absorption at 1940 nm and uric acid has more material absorption at 2120 nm.

For the purpose of one embodiment of the present invention, for example, existing Holmium:yttrium-aluminum-garnet (Ho:YAG) laser and thulium fiber laser (TFL) can be used as the laser source 20. Both wavelengths are in the spectrum of infrared which are highly absorbable by water. Other wavelengths absorbable by the ablation target can also be used for laser ablation. In one embodiment, a Ho:YAG laser is used, which has a wavelength of 2140 nm, pulse energy in a range from 0.01 to 6 joules (J), pulse frequency in a range from 5 to 120 Hz, and pulse duration in a range from 200 to 1200 microsecond ($\mu$s). In another embodiment, a thulium fiber laser is used, which has a wavelength of 1940 nm, pulse energy in a range from 50 to 100 mJ, pulse frequency in a range from 300 to 500 Hz, and pulse duration in a range from 150 to 1200 $\mu$s.

The power output of the laser source 20 is configured for laser ablation of stones 2, as well as for coagulation. In some embodiments, the power output of the laser may be ranged from a low power of 20-30 watts (W) to a high power of 100-200 W. The laser source 20 can have different operating modes, for example, ablation mode and coagulation mode. In the ablation mode, the power and pulse energy, frequency and duration may be controlled by the system, and specific settings may be selected by the user based on the need of a surgery. In some embodiments, the high power mode may provide higher frequency, such as 50-80 Hz with a Ho:YAG laser, while having the pulse energy as low as 0.2-0.3 J, depending on stone composition and location. Laser setting for ureteroscopic laser lithotripsy varies with stone density, stone volume and anatomical location of the stone, such as in the renal calyx, renal pelvis, ureter, or bladder. In the coagulation mode, typically a power output about 5-40 W is used for cauterizing or causing coagulation of veins at the surgical site to prevent or stop bleeding.

The laser fiber used for the laser ablation surgery is typically sterilized single use non-contact laser fiber. The fiber core diameter, the fiber tip dimension and the firing angle can be configured according to the need of the laser ablation surgery. The laser fiber for Ho:YAG laser may have a diameter of 200, 365, 550 and 1,000 micron ($\mu$m). The laser fiber for the thulium fiber laser is smaller in diameter and may have a diameter of 150, 200, 365, 550, 940 $\mu$m. The laser fiber is placed through a lumen, such as a working channel, of an endoscope 40, with one end of the laser fiber protruding from the distal end of the endoscope and the opposing end is connected to the laser source by a surgeon in a surgery.

The endoscope 40 has an elongated probe, an optical cable with a lens for viewing the surgical site and for imaging, and one or more lumens available to the user for guiding other instruments for surgical procedures, which are commonly referred to as operating or working channels. In various embodiments of retrograde ureteroscopic laser lithotripsy for treating urinary tract calculi, the endoscope 40 includes ureteroscope and cystoscope which is a continuous flow endoscope. Herein, the terms of ureteroscope and ureterorenoscope are used interchangeably.

In the case of ureteroscope, a port at the proximal end of the ureteroscope is used for feeding the irrigation fluid through a working channel for laser lithotripsy. In some embodiments, known endoscope structures, such as single channel ureteroscope, dual channel semi-rigid ureteroscope and dual channel flexible ureteroscope, can be used. In the case of cystoscope, the continuous flow endoscope has a flow sheath that includes an irrigation fluid inlet and irrigation fluid outlet disposed at the proximal end of the elongated probe. In one embodiment, the flow sheath includes an inner sheath and an outer sheath, disposed coaxially with each other, and the irrigation fluid inlet and outlet are connected to the proximal end of the outer sheath. It should be noted that the term of single channel or dual channel ureteroscope refers to the number of working channels or lumens available to a surgeon, for example, for placing laser fiber and other surgical tools and for feeding an irrigation fluid. The ureteroscope also has other designated channels, such as a channel for digital camera and a channel for light source, and these designated channels are not available for placing laser fiber or surgical tools or for feeding irrigation fluid. Therefore, herein the term of endoscope having one or more lumens refers to an endoscope having one or more working channels.

Figure 3:
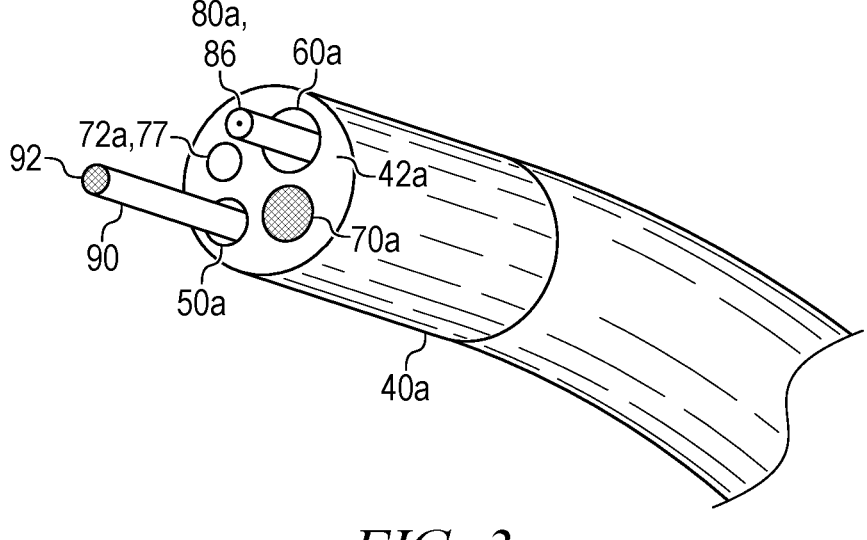
FIG. 3 is a schematic view of a dual channel ureteroscope in one embodiment of the present invention.

In various embodiments, endoscope 40 includes at least one temperature sensor 80 disposed at the distal end of the endoscope 40. FIG. 3 illustrates the distal end of a dual channel ureteroscope 40*a*, according to one example embodiment, which has two working channels as well as two designated channels. As shown, according the example, at distal end 42*a* of ureteroscope 40*a*, there are an optical channel 70*a* for camera and a light source channel 72*a* for fiber optic or LED light 77, which are designated for imaging and viewing and are sealed. In the example, there are two working channels 50*a*, 60*a* for inserting a laser fiber 90, a basket (not shown) for removal of stone fragments, or other surgical tools, and for delivering an irrigation fluid 4 to the surgical site. See FIGS. 5 and 6 for examples of delivering irrigation fluid 4 to the surgical site.

The working channels may have a diameter from 2 French to 7 French (1 French=0.33 mm). As shown, the laser fiber 90 is inserted through working channel 50*a* after the distal end of the ureteroscope is placed in the surgical site. The distal end or tip 92 of the laser fiber is typically extended about 4 to 5 mm beyond the distal end 42 of the ureteroscope. In the example, the irrigation fluid 4 is also fed through working channel 50*a*. According to various embodiments, irrigation fluid 4 can also, or alternatively, be fed through working channel 60*a*.

In the embodiment shown in FIG. 3, ureteroscope 40*a* has a temperature sensor 80*a* protruding from working channel 60*a*, disposed about 1 to 4 mm beyond the distal end 42 of the ureteroscope. In general, the temperature sensor 80*a* is positioned about 1 to 3 mm proximal to tip 92 of the laser fiber in the longitudinal direction of the ureteroscope, avoiding a direct contact with the tip 92 of the laser fiber 90. Temperature sensor 80*a* may be inserted through working channel 60*a* or predisposed in the working channel. The temperature sensor 80*a* may be removable or affixed.

Moreover, with the dual channel ureteroscope, either semi-rigid or flexible, the temperature sensor 80*a* may be disposed at the distal end of either working channel. The temperature sensor 80*a* is positioned about 1 to 3 mm proximal to the tip of the laser fiber in the longitudinal direction of the ureteroscope. In a single channel ureteroscope, the temperature sensor 80*a* may be disposed at the distal end of the single working channel, with the temperature sensor 80*a* positioned about 1 to 3 mm proximal to the tip of the laser fiber placed in the same channel. In various embodiments, the temperature sensor may be part of a multi-sensor device 86, which in addition to the temperature sensor can include other types of sensors, such as a flow sensor, a fluid pressure sensor, or any combination of sensors.

Figure 4:
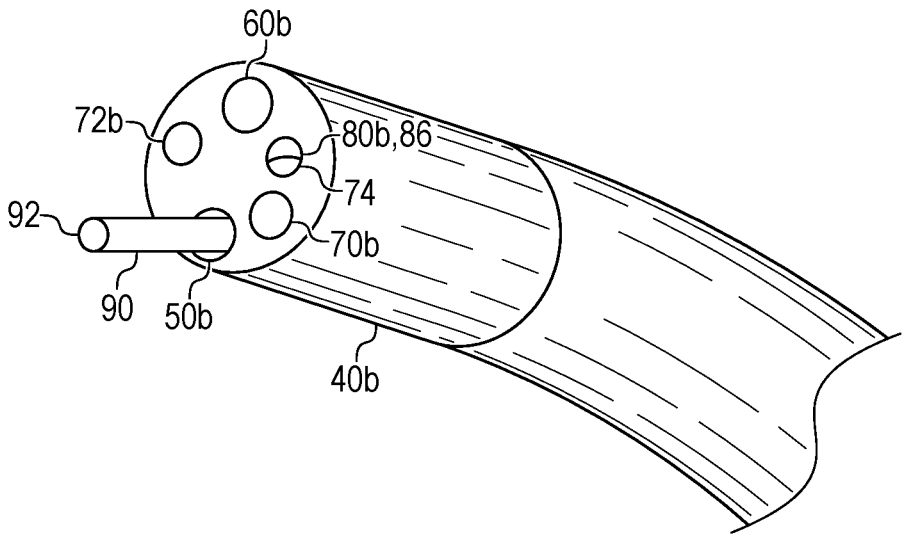
FIG. 4 a schematic view of a dual channel ureteroscope in another embodiment of the present invention

FIG. 4 illustrates another embodiment of a dual channel ureteroscope 40*b*, according to various embodiments of the present invention. As shown, the ureteroscope 40*b* has two working channels 50*b*, 60*b* and three designated channels. In addition to a designated optical channel 70*b* for camera and a designated light source channel 72*b* for fiber optic or LED light, the ureteroscope 40*b* has a designated temperature sensor channel 74 which holds a temperature sensor 80*b* therein. In various embodiments, the temperature sensor 80*b* may be part of a multi-sensor device 86, which in addition to the temperature sensor can include other types of sensors, such as a flow sensor, a fluid pressure sensor, or any combination of sensors.

As shown, temperature sensor 80*b* protrudes slightly, approximately 1 to 3 mm, from the surface of distal end 42*b* of the ureteroscope 40*b*. In such embodiment, the temperature sensor 80*b* is essentially built in the distal end of the ureteroscope 40*b*. When a laser fiber 90 is inserted through working channel 50*b*, temperature sensor 80*b* is about 1 to 3 mm proximal to the tip 92 of the laser fiber 90 in the longitudinal direction of the ureteroscope 40*b*. In this embodiment, working channel 60*b* remains available for surgical tools, or it can also be used to feed the irrigation fluid 4 in addition to working channel 50*b* if needed. Alternatively, the temperature sensor 80*b* may be incorporated into designated channel 70*b* or 72*b* without interfering with the function of the camera or the light source. Moreover, in a further embodiment of a dual channel ureteroscope, a wireless temperature sensor may also be built on the distal end of the ureteroscope. Similarly, in a single channel ureteroscope, in addition to an optical channel for camera and a light source channel for fiber optic or LED light, the single channel ureteroscope has a designated temperature sensor channel which holds a temperature sensor therein in the same manner shown in FIG. 4. Similarly, in the single channel ureteroscope, a wireless temperature sensor may also be built on the distal end of the ureteroscope.

Figure 5:
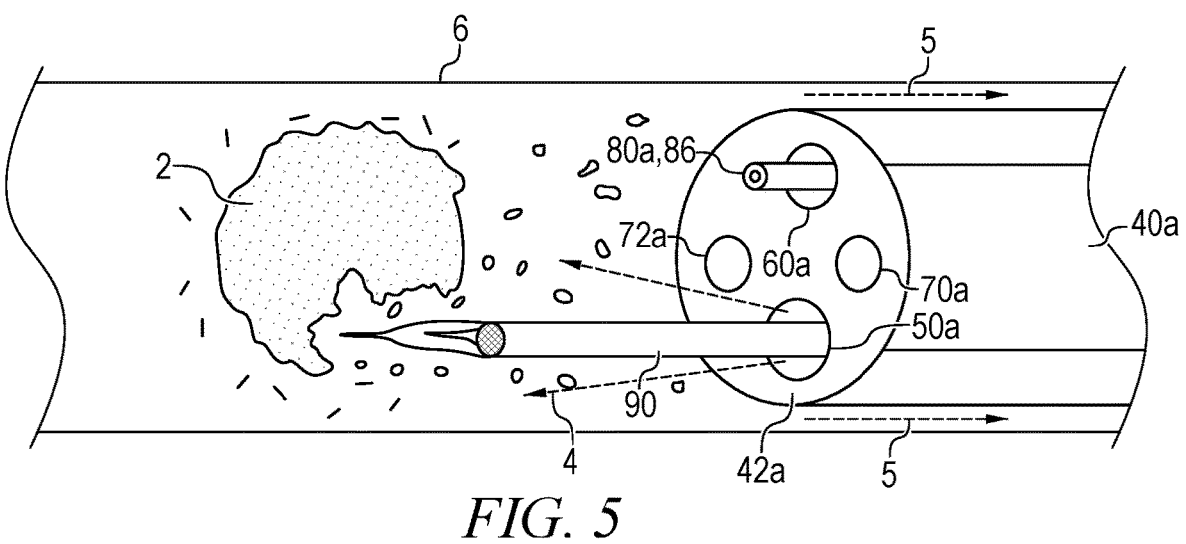
FIG. 5 is a schematic illustration of a laser lithotripsy surgery for treating a ureter stone using the system in one embodiment of the present invention.
Figure 6:
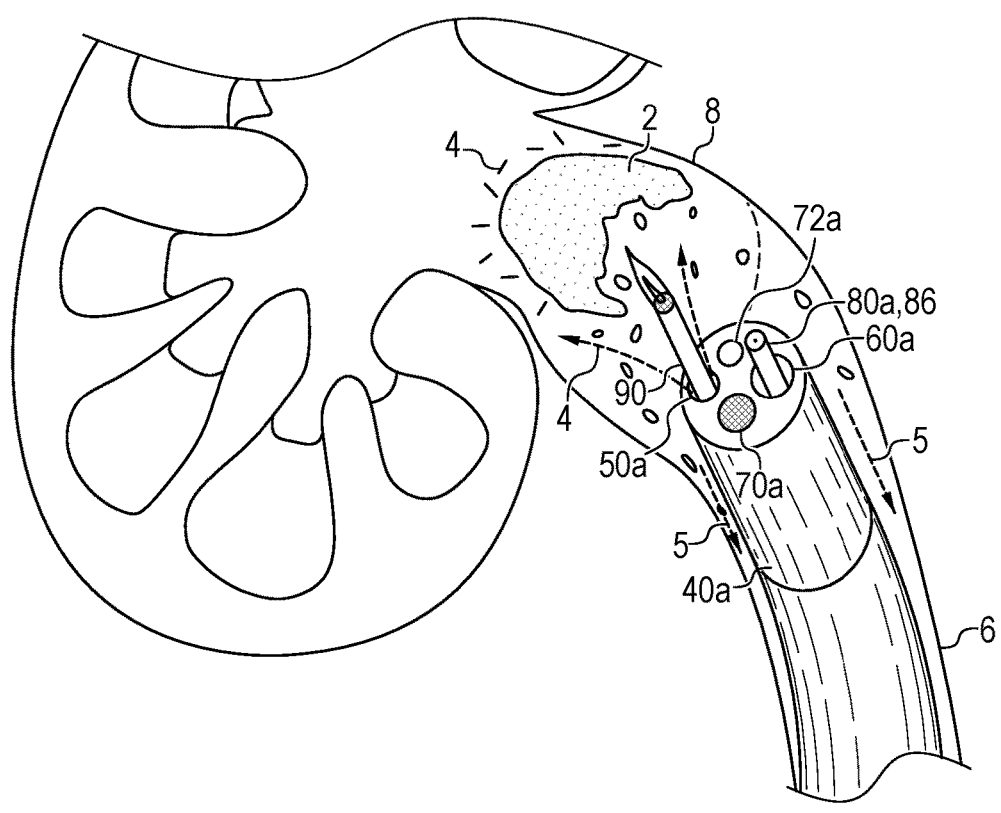
FIG. 6 is a schematic illustration of a laser lithotripsy surgery for treating a kidney stone using the system in one embodiment of the present invention.

Temperature sensor 80, 80*a*, 80*b* is structured to measure the temperature of an irrigation fluid at the surgical site of a laser ablation surgery in real time. As described above, ureteroscopic laser lithotripsy is performed with fluid irrigation. A sterile saline solution at room temperature can be used as the irrigation fluid 4. As illustrated in FIGS. 5 and 6, in ureteroscopic laser lithotripsy surgery for treating ureteral stone and kidney stone, respectively, a laser fiber 90 is inserted through a working channel 50*a*, 50*b* of ureteroscope 40*a*, 40*b*, respectively, and the tip 92 of the laser fiber 90 is positioned in direct contact with, or adjacent to, a stone 2 to be removed. In the process of laser ablation, the irrigation fluid 4 is continuously fed to the surgical site, which circulates around the stone 2 and absorbs heat generated by laser radiation.

The heated irrigation fluid 4 at the surgical site, according to various embodiments, exits naturally as a fluid outflow 5 along the outside surface of the ureteroscope antegrade within the lumen of the ureter 6 to the bladder, from which the effluent is drained through a bladder catheter. If a ureteral access sheath is used in the surgery, the heated irrigation fluid at the surgical site primarily flows out through the luminal space between the ureteral access sheath and the ureteroscope.

During laser radiation, the temperature of the irrigation fluid at the surgical site increases rapidly, in a matter of seconds. The soft tissue surrounding or adjacent to the stone, such as a renal pelvis 8, a renal calyx, or a ureter 6, is in near constant contact with the heated irrigation fluid during laser radiation. In the absence of sufficient pausing of laser radiation or sufficient irrigation, the temperature of the irrigation fluid at the surgical site can rise above a safe temperature range, which consequently can cause thermal injury to a patient. Therefore, the temperature of the irrigation fluid at the surgical site measured in real time by the temperature sensor reflects the temperature to which the surrounding soft tissue is exposed.

Temperature sensor 80 is operably connected to the system control 100 and temperature data is processed and utilized by the system control 100 for temperature control at the surgical site as further described below. Various known temperature sensors and sensing mechanisms, for example, thermocouples, thermistors, resistance temperature sensors, semiconductor sensors, particularly miniature sensors, can be used for the purpose of the present invention. The temperature sensor can also be wireless.

The temperature at the surgical site can be a function of laser power, frequency, pulse width, duration of laser radiation, the flow rate of the irrigation fluid, the temperature of the inflow irrigation fluid, stone composition and volume, as well as multiple individual anatomic features, such as diameter of the ureter at the surgical sites, degree of hydronephrosis, abnormal anatomy or renal perfusion, pre-stented ureter, etc.

In some embodiments, system control 100 comprises a patient injury risk calculator 102 for risk assessments and monitoring, and a laser control 110 for automated control of the laser source. Laser control 110 is operably connected to laser source 20. The patient injury risk calculator 102, also referred to as risk calculator, comprises one or more predetermined surgical site irrigation fluid temperature thresholds 202 (see FIG. 2) and a plurality of predetermined thermal injury risk factors 206 which are relevant to potential thermal injuries during laser ablation surgery. The risk of thermal injury to the soft tissue at the surgical site and potential postoperative complications can be a function of various factors, which are collectively identified by the system control as thermal injury risk factors 206. The thermal injury risk factors 206 as well as their attributes may include any one factor, or any combination of risk factors, selected from the following list: laser type and power, pulse energy, frequency and duration, irrigation fluid flow rate, inflow irrigation fluid temperature, stone volume, stone density, anatomic location of the stone, the degree or extent of elevated temperature of the irrigation fluid at the surgical site, duration of the exposure, cumulative time at elevated temperatures, the flow rate of irrigation fluid during the time of elevated temperature(s) being detected, efficiency of cooling by the irrigation fluid which may be affected by the location and anatomic structure of the surrounding soft tissue, such as confined vs relatively less restricted space for cooling, clinical significance of certain thermal injuries, and other relevant factors, such as preexisting ureteral stricture, impacted stone, interval time from prior laser lithotripsy and repetitive surgical site laser treatment. The predetermined surgical site irrigation fluid temperature thresholds and thermal injury risk factors may be preset by the manufacturer of the laser ablation system 10, or inputted or modified by the users (e.g., an operator of a laser ablation endoscope) according to the need of specific surgeries.

In some embodiments, one of the predetermined surgical site irrigation fluid temperature thresholds 202 is a critical surgical site irrigation fluid temperature, and another predetermined surgical site irrigation fluid temperature threshold is a warning surgical site irrigation fluid temperature. When the temperature of the irrigation fluid at the surgical site reaches the critical surgical site irrigation fluid temperature, the soft tissue at the surgical site is exposed to a critical temperature, beyond which the soft tissue will be subjected to thermal injury. The warning surgical site irrigation fluid temperature is below the critical surgical site irrigation fluid temperature, and the difference between the two temperatures can be determined empirically according to the surgical procedure to be performed. For example, in an example embodiment, the critical surgical site irrigation fluid temperature may be set at 43° C., which is considered as the upper safety temperature limit for the soft tissue, and the warning surgical site irrigation fluid temperature may be set at 41° C. The irrigation fluid used in ureteroscopic laser lithotripsy is typically maintained at room temperature, which is about 20 to 22° C. After intracorporeal delivery through the ureteroscope, the temperature of the irrigation fluid entering the surgical site will be higher than the room temperature but below normal body temperature which is about 36.1 to 37.2° C.

In some embodiments, system control 100 includes a microprocessor incorporating therein the predetermined surgical site irrigation fluid temperature thresholds 202 and the plurality of thermal injury risk factors 206 and their attributes. The microprocessor executes the patient injury risk calculator 102 for preoperative and real time monitoring and risk assessments, as will be described in more detail below.

Figure 2:
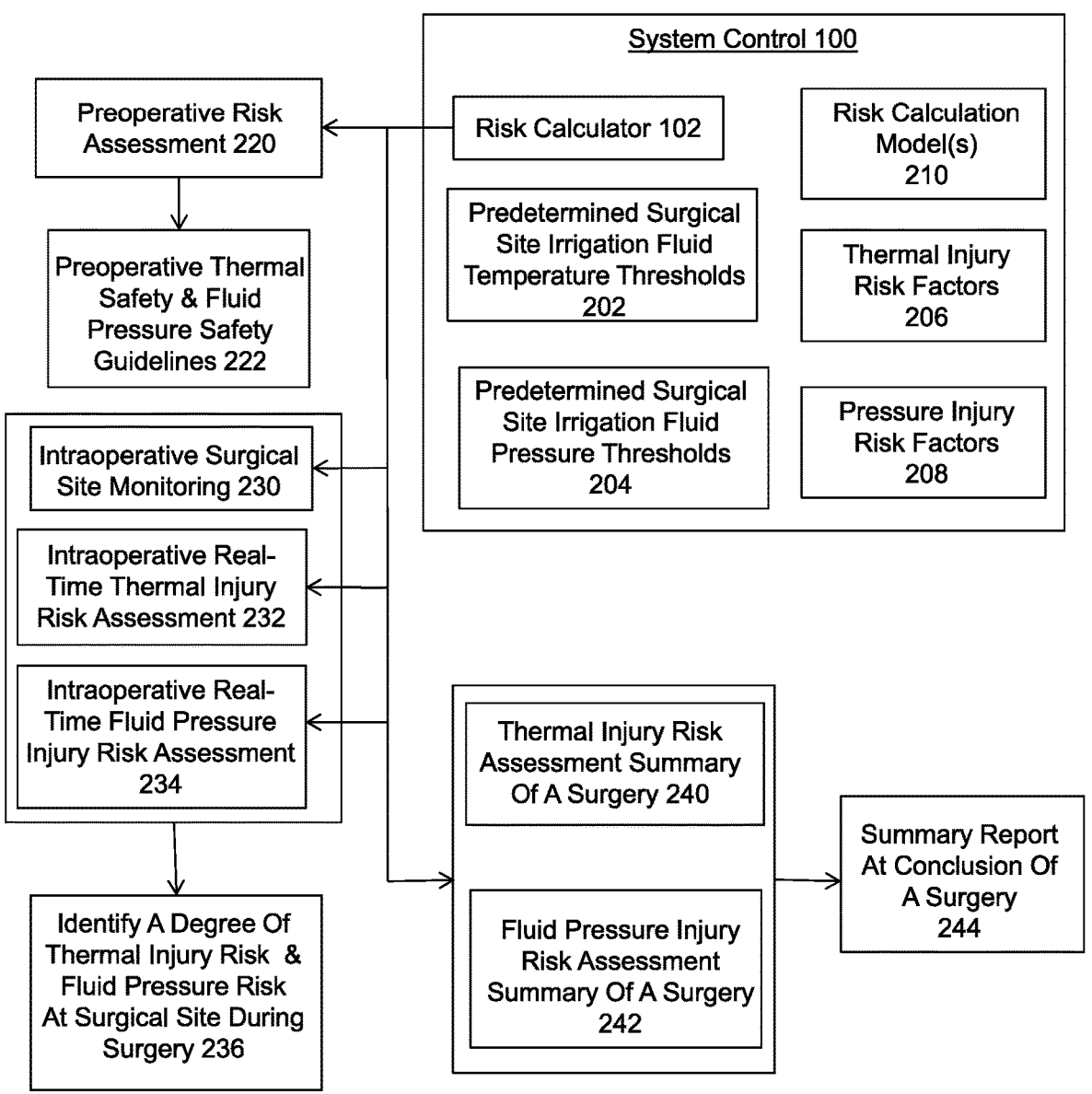
FIG. 2 is a schematic block diagram illustrating functions of the risk calculator of the system control of the laser ablation surgery system of the present invention.

As illustrated in FIG. 2, the patient injury risk calculator 102, according to various embodiments, can have several operating modes for providing safety measures in different stages of a laser ablation surgery. Moreover, the patient injury risk calculator 102 can have various operating modes for providing safety measures in different types of laser ablation surgery based on, for example, one or more of the following listed different types of: patient anatomy, medical history, laser ablation surgery equipment, surgical site parameters, etc. According to various embodiments, the variability of operating modes can be represented in the system control 100 by one or more risk calculation models 210 that, for example, can be stored in a memory storage repository that is communicatively coupled to at least one processor in the system control 100. In a preoperative risk assessment mode, the risk calculator 102 can be configured to perform a preoperative risk assessment, at step 220, according to the predetermined surgical site irrigation fluid temperature thresholds and user selected laser settings, such as laser power, pulse energy and frequency, pulse width, as well as specific pulse mode, such as Moses, stone volume, stone density, anatomic location of the stone, decision of treatment such as dusting or basketing, the irrigation fluid information, and other relevant information.

In preoperative risk assessment as well as in real time risk assessment described later below, the patient injury risk factors, which can include thermal injury risk factors 206 and their attributes, pressure injury risk factors 208 and their attributes, and other patient injury risk factors, may have different weighing (e.g., weight values) in terms of their relevance to an overall patient injury risk score or guideline. Weights applied to associated patient injury factors, according to various embodiments, represent a relative importance of each factor to other factors accounted for in a patient injury risk calculation model 210 to collectively model a patient injury risk score for a particular stage of a laser ablation surgery on a specific patient.

For example, with respect to thermal injury risks, while using a low power laser setting, high frequency pulses typically will have a higher weighing on the risk of rapidly generating heat than lower frequency pulses. The more rapidly that heat increases at a surgical site the higher the patient injury risk during a laser ablation surgery. Assuming all other factors, other than the thermal injury risk factors 206, in a patient injury risk calculation model 210 remain the same importance (weight), a patient injury risk calculation model 210 can apply a higher weight value to a thermal injury risk factor 206 representing a frequency of pulses in which higher frequency pulses vs. lower frequency pulses can increase a thermal injury risk probability of causing patient injury during a particular stage of a laser ablation surgery. That is, for example, as the frequency of pulses is increased to a thermal injury threshold and entering into a warning range, the model 210 may be changed to use a higher weight value applied to the thermal injury risk factors 206 associated with increasing frequency pulses. The thermal injury risk factors 206 associated with a frequency of pulses, accordingly with a higher weight value, would increase a patient injury risk score calculation for a particular stage of a laser ablation surgery on a specific patient.

In the example above, the preoperative risk assessment produces a preoperative thermal safety guideline, at step 222, which may include a patient injury risk score, to the operating surgeon on laser deployment as well as on irrigation fluid management. For example, the preoperative thermal safety guideline may recommend a maximum time of a continuous laser radiation or frequency of pausing laser radiation to prevent overheating, the duration of laser pausing time to allow the irrigation fluid to cool down the surgical site between segments of laser radiation, and a minimum flow rate of the irrigation fluid to dissipate heat at the surgical site. The preoperative thermal safety guideline may be displayed on a user interface of the system during the surgery, which assists surgeons to carry out the laser ablation procedure using proper safety measures.

In similar fashion to that discussed above with respect to thermal injury risk factors 206, with respect to fluid pressure injury risks, the fluid pressure injury thresholds 204 and the fluid pressure injury risk factors 208 can be used by a patient injury risk calculation model 210 to calculate an overall score representing a patient injury risk for particular stage of a laser ablation surgery on a specific patient. For example, if irrigation fluid flow to a surgical site is increased to a fluid pressure injury threshold and entering into a warning range, a patient injury risk calculation model 210 can apply a higher weight value to a fluid pressure injury risk factor 208 representing an increasing irrigation fluid flow at the surgical site. The higher amount of fluid flow to the surgical site, under certain surgical parameters and constraints, will predictably increase fluid pressure at the surgical site. That is, for example, as the irrigation fluid flow to the surgical site is increased, this can result in an increase in fluid pressure at the surgical site under certain surgical conditions. As the fluid pressure increases to a fluid pressure injury threshold and enters into a warning range, the model 210 may be changed to use a higher weight value applied to the fluid pressure injury risk factors 208 associated with increased fluid flow to the surgical site and thereby increasing fluid pressure at the surgical site. The fluid pressure injury risk factors 208, accordingly with a higher weight value, would increase a patient injury risk score calculation for a particular stage of a laser ablation surgery on a specific patient.

Once a laser ablation surgery starts, system control 100 activates the risk calculator's intraoperative surgical site monitoring mode, at step 230. The risk calculator 102 actively monitors the temperature of the irrigation fluid at the surgical site detected by temperature sensor 80. The risk calculator 102 also can actively monitor the fluid flow rate of the irrigation fluid to the surgical site detected by at least one flow sensor 120. The risk calculator 102 also can actively monitor the fluid flow rate of fluid outflowing from the surgical site detected by at least one flow sensor 120. The risk calculator 102 also can actively monitor the fluid pressure of the irrigation fluid at the surgical site detected by at least one fluid pressure sensor 140.

If the risk calculator indicates, for example, that the temperature of the irrigation fluid at the surgical site has reached a warning surgical site irrigation fluid temperature, the system control sends a warning signal to alert the user. The warning signal can be a light or an audio signal. Moreover, the system control may automatically activate laser control 110 to reduce the power output of the laser source to allow the surgical site to be cooled down by the irrigation fluid. However, an operator of the system 10 and the laser source 20 can manually override this automatic reduction of power. For example, the surgeon can decide to override the automatic control and thereby manually operate the laser to cauterize veins and control bleeding by using the laser during the laser ablation surgery on a specific patient.

If the temperature sensor 80, 80a, 80b, senses that the temperature of the irrigation fluid 4 at the surgical site has reached a critical surgical site irrigation fluid temperature, for example 43° C., the system control 100 may activate laser control 110 to stop emission from laser source 20 to prevent further rising of temperature of the irrigation fluid at the surgical site. Moreover, at the critical surgical site irrigation fluid temperature, the system control may further send one or more warning signals to inform the presence of the critical surgical site irrigation fluid temperature to the surgeon, as well as to indicate stopped laser emission due to the critical surgical site irrigation fluid temperature.

Moreover, once a laser ablation surgery starts, the risk calculator 102 further operates in its intraoperative patient injury risk assessment mode. The risk calculator is configured to perform a real time thermal injury risk assessment, at step 232, during the laser ablation surgery. In certain embodiments, the risk calculator is configured to perform a real time fluid pressure injury risk assessment, at step 234, during the laser ablation surgery.

Using the above described thermal injury risk factors 206, the risk calculator 102 evaluates potential thermal injury risks with the information acquired by the temperature sensor 80 during the laser ablation procedure. For example, the risk calculator 102 can evaluate whether the soft tissue at the surgical site is exposed to an elevated temperature above the critical surgical site irrigation fluid temperature, how long it is exposed to, and the speed or time that the irrigation fluid sufficiently cools the surgical site. Further in consideration of other thermal injury factors, such as the anatomic location and structure of the soft tissue exposed to the elevated temperature and clinical significance of a particular thermal injury, the risk calculator determines the degree of thermal injury risk at the surgical site during the laser ablation surgery. In an example embodiment, the risk calculator 102, using the risk calculation models 210, can determine an overall patient injury risk score. The risk calculator 102, using the risk calculation models 210, can also determine a thermal injury risk score that qualifies a thermal injury risk, which is herein referred to as a qualifying thermal injury risk score. According to various embodiments, the risk calculator 102 using the risk calculation models 210 can determine a fluid pressure injury risk score that qualifies a fluid pressure injury risk at the surgical site, which is herein referred to as a qualifying fluid pressure injury risk score.

In one embodiment, the thermal injury risk score may be expressed by a risk scale, for example in a scale of 1-10. In such an example, a score of above 5 may be identified as a qualifying thermal injury risk score. The higher the score is indicates the higher probability of thermal injury. In certain embodiments, the fluid pressure injury risk score may be expressed by a risk scale, for example in a scale of 1-10. In such an example, a score of above 5 may be identified as a qualifying fluid pressure injury risk score. The higher the thermal injury risk score is indicates the higher probability of thermal injury. The higher the fluid pressure injury risk score is indicates the higher probability of fluid pressure injury at the surgical site. An overall patient injury risk score can also be calculated which may be, in one example embodiment, a combination of the thermal injury risk score and the fluid pressure injury risk score.

The qualifying thermal injury risk score, the qualifying fluid pressure injury risk score, and the patient injury risk score, can be displayed in real time on a user interface of a computer processing system during the surgery, as well as at the conclusion of the surgery. The qualifying thermal injury risk score, the qualifying fluid pressure injury risk score, and the patient injury risk score, may be displayed numerically or graphically, and may also be displayed with light or audio signals. Furthermore, the attributes of the qualifying thermal injury risk score, such as a prolonged laser radiation time or a rapid rising temperature under a high pulse energy setting, may also be displayed to assist in identifying corrective actions. Similarly, the attributes of the qualifying fluid pressure injury risk score may also be displayed to assist in identifying corrective actions. Alternatively, all scores, for example, from 1-10, may be all displayed, with an indication of different degree of the risk, at step 236.

Moreover, at the conclusion of a laser ablation surgery, the risk calculator may summarize intraoperative thermal injury risk assessment, at step 240, intraoperative fluid pressure injury risk assessment, at step 242, and overall patient injury risk assessment, during the surgery and provide a summary report, at step 244. The summary report may indicate a presence or absence of a high degree of thermal injury risk during the surgical procedure, such as a presence or absence of a qualifying thermal injury risk score during the surgical procedure, and may also provide relevant attributes resulting in the qualifying thermal injury risk score. The summary report, similarly, may indicate a presence or absence of a high degree of fluid pressure injury risk during the surgical procedure and may also provide relevant attributes resulting in the qualifying fluid pressure injury risk score. The display of the user interface may designate a safety section in which the preoperative risk assessment, the intraoperative injury risk assessment result, and the summary report, are all shown.

The summary report, at step 244, may present to the surgeon a summary report of thermal/pressure injury risk factors at the surgical site. One or more examples of factors that can be provided in a summary report may include, but are not limited by, the following list of example factors:

a) Laser frequency/power and settings;
b) Inflow irrigation rate;
c) Inflow irrigation temperature;
d) Operator duty cycle (pattern of laser activation over one minute);
e) Measured irrigation temperature at surgical site (number of events);
f) Duration of irrigation temperature on each event;
g) Number of events irrigation temperature reached where than 45 degrees Celsius less than 50 degrees Celsius;
h) Extent of peak temperature;
i) Cumulative exposure minutes greater than 43 degrees Celsius;
j) Measured intrapelvic pressure (IPP) greater than 30 centimeters of water events;
k) Duration of intrapelvic pressure greater than 30 centimeters of water on each event;
l) Number of events intrapelvic pressure greater 37 cm water less than 50 centimeters of water;
m) Extent of peak IPP greater than 37 years of water;
n) Extent of peak intrapelvic pressure greater than 40 centimeters of water;
o) Cumulative exposure minutes greater than 30 centimeters of water; and
p) Presence or absence of ureteral access sheath during ureteroscopy.

The qualifying thermal injury risk score associated with a surgery can be utilized by the operating surgeon intraoperatively and postoperatively. During the surgery, if a qualifying thermal injury risk score is indicated by the system, the surgeon can take timely actions to mitigate further risks, such as shortening laser radiation time, increasing duration of the pause, or increasing flow rate of the irrigation fluid. The qualifying fluid pressure injury risk score associated with a surgery can be utilized by the operating surgeon intraoperatively and postoperatively. During the surgery, if a qualifying fluid pressure injury risk score is indicated by the system, the surgeon can take timely actions to mitigate further risks, such as shortening the time of, or temporarily halting, the laser ablation procedure time, increasing duration of a pause, or decreasing irrigation fluid inflow 4 to the surgical site or increasing fluid outflow 5 from the surgical site.

Postoperatively, if a qualifying thermal injury risk score is indicated by the system for the surgical procedure, the surgeon will be alerted to take precautionary actions for postoperative management, for example, possible stent placement, interval imaging, laboratory tests and additional postoperative instructions to the patient. Similarly, based on a qualifying fluid pressure injury risk score indicated by the system for the surgical procedure, the surgeon will be alerted to take precautionary actions for postoperative patient management and additional postoperative instructions to the patient. With the knowledge of a potential risk and proactive postoperative management, it assists surgeons to prevent severe adverse clinical complications, particularly when the earlier postoperative symptoms are mild.

In a further embodiment, the system may further comprise a temperature sensor for monitoring the irrigation fluid temperature before it enters the endoscope, which may be referred to as an inflow temperature sensor. The inflow temperature sensor is fluidly connected to the inflow irrigation fluid prior to the irrigation fluid entering the endoscope, such as disposed in the irrigation fluid reservoir or connected to the port of the endoscope through which the irrigation fluid is fed. The inflow temperature sensor is operably connected to system control 100 and data collected from inflow temperature sensor is processed and utilized by the system control for risk assessments as described above. The risk calculator may further comprise predetermined temperature criteria for inflow irrigation fluid. Moreover, system 100 may further comprise a temperature regulating device configured to adjust the temperature of the irrigation fluid before it enters the endoscope. Various known temperature regulating mechanisms can be used for the present system. In some embodiments, a semiconductor peltier may be used to regulate the irrigation fluid temperature prior to feeding into the endoscope. Consistency in the temperature of inflow irrigation fluid reduces complexity or variations in controlling the temperature at the surgical site.

In some embodiments, the present laser ablation surgery system may include one or more irrigation flow sensors 120 fluidly connected to one or more lumens of the endoscope for monitoring the inflow of the irrigation fluid 4 into the surgical site, the outflow of fluid 5 from the surgical site, or both, during a laser ablation surgery. In one embodiment, one or more irrigation flow sensors 120 may be disposed within the flow path of the inflow irrigation fluid to monitor the flow rate of the irrigation fluid fed to the surgical site during the surgery. The flow sensor may be disposed at the inlet of a working channel of the endoscope which is used to feed the irrigation fluid or within the working channel, or within the irrigation fluid feeding tube leading to the endoscope. A flow sensor may be disposed at a fluid inlet port of a working channel at the distal end of the endoscope which is used to suction/siphon, or simply allow gravity to discharge, the fluid from the surgical site via a working channel, or within a fluid discharge tube leading from the endoscope. The irrigation flow sensors are operably connected to system control 100 and flow data collected from irrigation flow sensors 120 is processed and can be utilized by the system control for temperature control, and optionally also for pressure control, at the surgical site.

The risk calculator's intraoperative surgical site monitoring mode, according to certain embodiments, may further include real time flow monitoring. The risk calculator further comprises one or more predetermined irrigation flow criteria, and the system control is configured to activate the laser control 110 when the risk calculator indicates a violation of the predetermined irrigation flow criteria. In one embodiment, the predetermined irrigation flow criteria is a minimum flow rate of the inflow irrigation fluid while the laser is emitted to the ablation target. If the risk calculator indicates that the flow rate of the irrigation fluid is below the minimum flow rate, laser control 110 is activated to stop or reduce emission from the laser source 20. Moreover, the system control 100 may also send a signal to inform the user about the stopped or reduced laser emission due to insufficient irrigation. In the event if the irrigation fluid has run out, or the irrigation fluid is restricted for some reason or mistakenly or unintentionally turned off during a laser ablation surgery, further laser radiation will cause a substantial increase of the temperature of the irrigation fluid at the surgical site, which will cause irreversible thermal injury to the surrounding soft tissue. In this type of adverse events, the operating surgeon will be promptly alerted by the system to take timely actions to ensure adequate irrigation supply and to control the temperature at the surgical site.

Furthermore, one of the predetermined irrigation flow criteria can be a warning flow rate of the inflow irrigation fluid while the laser is emitted to the ablation target. If the risk calculator indicates the flow rate of the irrigation fluid reaching the warning flow rate, but not the minimum flow rate yet, the system control 100 may send a warning signal so that an earlier preventative action can be taken by the surgeon.

Moreover, in the intraoperative thermal injury risk assessment, the risk calculator 102 processes data received from irrigation flow sensors 120 in the process of determining the degree of thermal injury risk. The risk calculator 102 may identify certain irrigation flow conditions which will lead to rapid rising temperature at the surgical site in determining qualifying thermal injury risk score in the exemplary embodiment described above. For example, when the flow rate of the irrigation fluid decreases to a certain level, the irrigation fluid temperature at the surgical site has increased, but not reached the critical surgical site irrigation fluid temperature yet. However, under such condition, one long laser radiation will cause the temperature to reach or exceed the critical surgical site irrigation fluid temperature. The risk calculator may produce a qualifying thermal injury risk score with its attributes to indicate such an imminent risk.

In some embodiments, the system control 100 may further comprise a flow control 130 configured to adjust a flow rate of the irrigation fluid. When the risk calculator indicates a violation of the predetermined irrigation flow criteria or the temperature of the irrigation fluid at the surgical site reaching the predetermined surgical site irrigation fluid temperature threshold, the system control may activate flow control 130 to increase the flow rate of the irrigation fluid, or alert the user to adjust the flow rate.

Various flow regulating mechanisms can be used for the present system. In some embodiments, the irrigation fluid may be provided using a fluid inflow pump 133 connected to an irrigation fluid reservoir and the flow rate of the irrigation fluid delivered to the surgical site through the ureteroscope 40 is regulated. The pump 133 is operably connected to the flow control 130. In some embodiments, the irrigation fluid 4 is delivered from a flexible irrigation fluid bag as commonly used in laser lithotripsy surgeries through one or more channels of the ureteroscope to the surgical site. The pressure applied to the irrigation fluid bag through a pressure cuff or pressure bag sleeve may be automatically adjusted to maintain a stable flow rate of the irrigation fluid during a surgery. When the risk calculator indicates the flow rate of the irrigation fluid is at the warning or minimum flow rate, the pressure applied to the irrigation fluid bag can be increased to enhance the inflow of the irrigation fluid to the surgical site.

Physiological intra-renal pressure ranges from 5 to 10 cm $H_2O$ and the intra-renal pressure is increased during endoscopic surgery. 40 cm $H_2O$ is considered as the upper safety limit for intra-operative pressure. Complication rate increases under higher intra-renal pressure conditions. In some embodiments, the system 10 may further comprise one or more pressure sensors 140 communicatively coupled with the system control 100. The one or more pressure sensors 140 can be fluidly connected to the irrigation fluid 4 for monitoring inflow irrigation fluid pressure during a laser ablation surgery. The one or more pressure sensors 140 can be fluidly connected to the fluid outflow 5 for monitoring outflow fluid pressure during a laser ablation surgery. The one or more pressure sensors 140 can be located at the distal end of the endoscope 400 and can be fluidly connected to the fluid at the surgical site for monitoring fluid pressure at the surgical site during a laser ablation surgery.

In one embodiment, a pressure sensor may be disposed within the flow path of the inflow irrigation fluid 4 to monitor the pressure of the irrigation fluid fed to the surgical site during the surgery. Alternatively, in some embodiments, at least one flow sensor 120 can be configured to further measure the fluid pressure. In other words, the flow sensor 120 may function to measure both flow rate and fluid pressure. The pressure sensors 140 are operably connected to system control 100 and fluid pressure data collected from pressor sensors is processed and utilized by the system control 100.

The risk calculator 102, according to various embodiments, may further comprise one or more predetermined irrigation fluid pressure thresholds 204, which may be set at different levels depending on the location of the surgical site, such as in the kidney, ureter or bladder. When the risk calculator 102 indicates the pressure of inflow irrigation fluid 4, pressure of outflow fluid 5, or fluid pressure at the distal end of the endoscope at the surgical site, or a combination thereof, reaches a predetermined fluid pressure threshold, then flow control 130, and inflow pump 133 in certain embodiments, can be activated to regulate the irrigation fluid 4, such as to reduce inflow. Also, in certain embodiments, outflow pump control 135 and suction/siphon pump 7, can be activated to regulate the outflow fluid 5, such as to increase fluid outflow. Moreover, the system control 100 may further activate laser control 110 to stop laser emission during the process of adjusting pressure to avoid potential thermal injury in case of insufficient irrigation (e.g., fluid flow) at the surgical site.

System 100 can be fully automated to monitor and control the temperature of the irrigation fluid at the surgical site, flow rate of the irrigation fluid, and internal fluid pressure, and control laser emission according to the criteria and mechanisms described above.

Moreover, system 100 may further include an override mode, which allows the surgeon to override the laser control 110 under certain circumstances. For example, if the surgeon observes bleeding at the surgical site, while system control 100 might have stopped the emission from the laser source 20 because the irrigation fluid reaches a predetermined surgical site irrigation fluid temperature threshold, the surgeon can use the override mode to turn the laser source back ON at a lower power output for hemostasis and use the coagulation mode of the system to timely cauterize the veins and control bleeding.

The operation of laser ablation surgery system 100 is further described in reference to an example retrograde ureteroscopic laser lithotripsy for treating a kidney stone, as illustrated in FIGS. 3 and 6. The system 100 has a Ho:YAG laser with an emission wavelength of 2140 nm and a dual channel flexible ureteroscope, as shown in FIG. 3. In the laser lithotripsy surgery, as illustrated in FIG. 6, the distal end of the ureteroscope is placed into the renal pelvis 8 and a 200 μm laser fiber 90 is inserted through the working channel 50a of the ureteroscope with the tip 92 of the laser fiber in contact with the stone 2. The tip 92 of the laser fiber is extended about 4 to 5 mm beyond the distal end 42a of the ureteroscope. The dual channel flexible ureteroscope 40a has a temperature sensor 80a in the working channel 60a disposed at the distal end of the ureteroscope for measuring the temperature of the irrigation fluid at the surgical site during the procedure. The temperature sensor 80a is positioned about 1 to 3 mm proximal to tip 92 of the laser fiber in the longitudinal direction of the ureteroscope. In various embodiments, the temperature sensor may be part of a multi-sensor device 86, which in addition to the temperature sensor can include other types of sensors, such as a flow sensor, a fluid pressure sensor, or any combination of sensors.

Figure 1A:
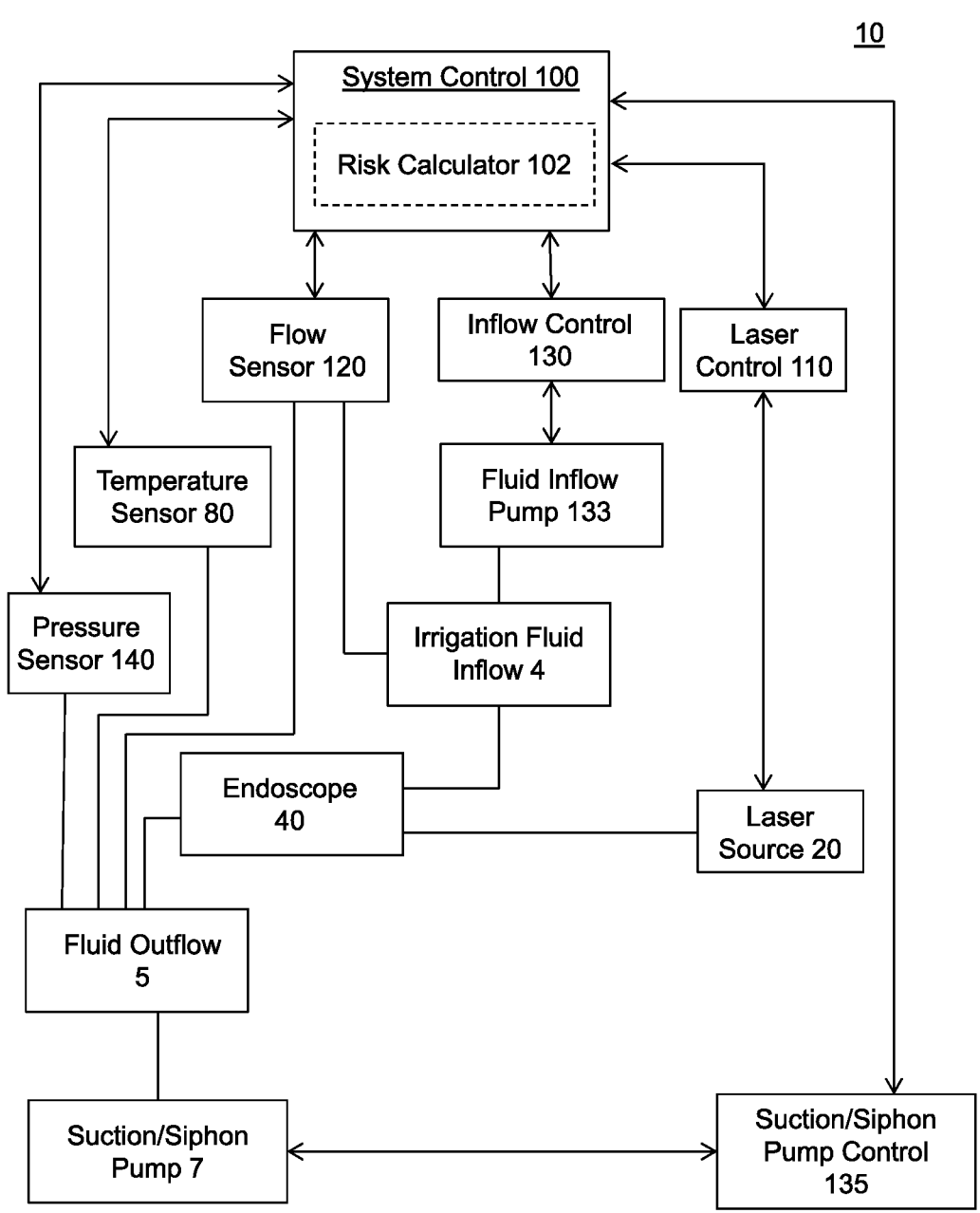
FIG. 1A is a schematic block diagram of the laser ablation surgery system in a further embodiment of the present invention.

A sterile saline solution is used as irrigation fluid 4 and is fed through the working channel 50a to the surgical site. The inflow of the irrigation fluid, according to certain embodiments, is driven by gravity and pressurized bag and regulated with a regulating clamp. In various embodiments, the inflow of the irrigation fluid can be driven by the inflow control 130 and the inflow pump 133, as illustrated in FIG. 1A.

The outflow 5 of the fluid from the surgical site can flow, according to certain environments, naturally along the outside surface of the ureteroscope to the bladder, as driven by the flow pressure due to the gravity driven inflow. One or more irrigation flow sensors 120 may be fluidly connected to the inflow of the irrigation fluid. In various embodiments, the fluid outflow 5, e.g., fluid flowing from the surgical site, can be driven by the suction/siphon pump control 135 and the suction/siphon pump 9. The fluid outflow 5 can optionally be through one or more of the working channels in the ureteroscope.

After the surgeon has selected laser power, pulse energy, pulse frequency and pulse duration through a user interface of a computer processing system in the system 10, based on the volume, density, and anatomic location of the stone and intended treatment, dusting or basketing, and other relevant information, the risk calculator 102 of the system control 100 automatically performs a preoperative risk assessment using the predetermined surgical site irrigation fluid tem- perature thresholds, thermal injury risk factors and their associated weighing as described above. The preoperative risk assessment can also use the surgical site fluid pressure thresholds 204, fluid pressure injury risk factors 208 and their associated weighing as described above. The system, according to various embodiments, generates a preoperative thermal safety guideline to the surgeon on laser deployment as well as management of irrigation fluid, including recommended maximum time of a continuous laser radiation or frequency of pausing, duration of pause of laser radiation, a minimum flow rate of the irrigation fluid, and other relevant intraoperative safety measures. The system, according to various embodiments, can generate a preoperative fluid pressure safety guideline to the surgeon regarding fluid flow management of irrigation fluid inflow 4 and fluid outflow 5.

In the laser lithotripsy surgery, the laser source 20 emits a laser beam through laser fiber 90 directly onto the kidney stone to fragment the stone. With an initial laser ablation of a large stone of 10 to 20 mm for approximately 1-5 minutes, depending on the density and volume of the stone, the large stone is fragmented to smaller pieces. Then, the laser is kept discharging repeatedly within an enclosed space. Under the laser impact, the fragments will bounce within renal pelvis and the renal calyx. As the fragments come into contact with the laser fiber, the fragments are further broken down until they are reduced to 1 to 2 mm, which are sufficiently small to flush out and to pass on their own. This process may take up to 10-15 minutes.

During this process, the fragments may often migrate after laser impact, which is referred to as stone retropulsion. It is understood that upon activation of pulsed laser, the irrigation fluid surrounding the laser tip evaporates and expands a vapor bubble and then collapses which cause unwanted movement of stone away from the tip of the laser fiber. As a result of stone retropulsion, retrograde manipulation and repositioning of ureteroscope further in the proximal ureter or into the renal pelvis ("chasing" the migrated stone) are often required. As such, further laser ablation occurs at one or more different locations in the renal pelvis or in the renal calyx. Each different location is a different surgical site. Therefore, the thermal impact to the soft tissue in the renal pelvis in one surgical procedure may occur at more than one locations in the urinary tract.

During the ureteroscopic laser lithotripsy, temperature sensor 80a measures the temperature of the irrigation fluid at the surgical site in real time and the risk calculator actively monitors the temperature detected by temperature sensor 80a for intraoperative surgical site monitoring as well as intraoperative thermal injury risk assessment, as described above. If the risk calculator indicates the temperature of the irrigation fluid at the surgical site reaches a predetermined surgical site irrigation fluid temperature threshold, system control 100 immediately takes preventative actions, such as issuing warning signals or activating laser control 100 to stop laser emission. Thus, the operating surgeon can take timely actions to mitigate the thermal injury risk as described above. Moreover, during the laser lithotripsy procedure the flow sensor 120 measures the flow rate of the irrigation fluid inflow 4 and the fluid outflow 5 in real time and the risk calculator actively monitors the flow rate detected by the one or more flow sensors 120. If the risk calculator 102 indicates a violation of the predetermined irrigation flow criteria, the system control may immediately issues a warning signal and/or activates the laser control 110 to stop laser emission as described above. Furthermore, during the laser lithotripsy procedure the one or more pressure sensors 140 measure the fluid pressure at the surgical site in real time and the risk calculator actively monitors the fluid pressure detected by the one or more pressure sensors 140. If the risk calculator 102 indicates a violation of the predetermined fluid pressure criteria, the system control 100 may immediately issue a warning signal and/or activate the laser control 110 to stop laser emission as described above.

Furthermore, during the laser lithotripsy procedure the risk calculator 102 performs intraoperative thermal injury assessment using predetermined thermal injury risk factors 206 and real time data from temperature sensor 80a as described above. If the risk calculator indicates a high degree of thermal injury risk at the surgical site, such as identifies a qualifying thermal injury risk score, then the system immediately displays the qualifying thermal injury risk score during the laser lithotripsy procedure to alert the operating surgeon, and may also activate laser control 110 to stop laser emission. The qualifying thermal injury risk score can be utilized by the surgeon intraoperatively to timely mitigate the thermal injury risk as described above.

Additionally, during the laser lithotripsy procedure the risk calculator 102 can perform intraoperative fluid pressure injury assessment using predetermined fluid pressure injury risk factors 208 and real time data from fluid pressure sensor 140a as described above. If the risk calculator indicates a high degree of fluid pressure injury risk at the surgical site, such as identifies a qualifying fluid pressure injury risk score, then the system immediately displays the qualifying fluid pressure injury risk score during the laser lithotripsy procedure to alert the operating surgeon, and may also activate laser control 110 to stop laser emission. The qualifying fluid pressure injury risk score can be utilized by the surgeon intraoperatively to timely mitigate the fluid pressure injury risk as described above.

At the conclusion of the laser lithotripsy procedure, the system provides an intraoperative thermal injury risk assessment summary report. The summary may indicate a presence or absence of a qualifying thermal injury risk score during the surgical procedure and may also provide relevant attributes resulting in the qualifying thermal injury risk score. The result of the intraoperative thermal injury risk assessment, particularly the qualifying thermal injury risk score, can be used by the surgeon for postoperative management as described above. Similarly, at the conclusion of the surgical procedure, the system provides an intraoperative fluid pressure injury risk assessment summary report. The summary may indicate a presence or absence of a qualifying fluid pressure injury risk score during the surgical procedure and may also provide relevant attributes resulting in the qualifying fluid pressure injury risk score. The result of the intraoperative fluid pressure injury risk assessment, particularly the qualifying fluid pressure injury risk score, can be used by the surgeon for postoperative management as described above.

In a further embodiment, the present invention further provides a method of laser ablation surgery that improves laser operation safety using existing endoscope and laser equipment. In this embodiment, an existing endoscope such as a dual channel flexible ureteroscope is used with a temperature sensor disposed at the distal end of the ureteroscope. A laser fiber is inserted through the first working channel, with its tip protruding about 4 to 5 mm from the distal end of the ureteroscope and with the opposing end connected to a laser source. The irrigation fluid is also fed through the first working channel to the surgical site. The temperature sensor may be placed through the second working channel and disposed about 1 to 4 mm proximal to the tip of the laser fiber in the longitudinal direction of the ureteroscope. The temperature sensor being configured to monitor the temperature of the irrigation fluid at the surgical site during the laser ablation surgery. During a laser ablation surgery such as an ureteroscopic laser lithotripsy, the surgeon can monitor the temperature of the irrigation fluid at the surgical site using the temperature sensor. If the temperature sensor detects the temperature of the irrigation fluid at the surgical site reaching a predetermined surgical site irrigation fluid temperature threshold, such as the critical surgical site irrigation fluid temperature set at 43° C., then the surgeon can immediately stop laser emission and take timely actions, such as adjusting laser settings or modifying or improving irrigation conditions. This would prevent a potential thermal injury to the soft tissue.

The laser ablation surgery system and the method of the present invention are particularly advantageous in several aspects. In current laser lithotripsy surgeries, surgical equipment and devices including the endoscope, digital camera and associated illumination/monitoring equipment, the laser system, and irrigation system are all separate devices, which are assembled together by the operating room staff at the start of a surgery. The existing laser system manufacturers may provide recommended laser settings for different laser lithotripsy procedures depending on the anatomic location of the stone and desired treatment such as dusting or basketing. However, safety measures during the laser lithotripsy surgeries are seriously lacking. Currently, no surgical laser system provides monitoring of the temperature at the surgical site to which the surrounding soft tissue is exposed during laser ablation. Despite the fact that the laser lithotripsy procedure requires uninterrupted irrigation, no surgical laser system monitors and coordinates irrigation with the laser emission during the laser ablation procedure, and the existing laser system and irrigation system operate independently.

With the current laser surgery equipment, the responsibility of safe laser ablation during lithotripsy procedures essentially falls on the shoulders of operating surgeon and operating room (OR) staff. Intraoperatively, the surgeon has the responsibility to anticipate and manage potential safety hazards, such as inappropriate laser settings, prolonged uninterrupted laser radiation, loss of irrigation during laser radiation, and not cognizant of the endoscope manual valve positions on low or the off position during laser ablation. A common practice of experienced urologists is to take frequent breaks during laser ablation in an effort to avoid potential overheating at the surgical site. However, this is done without knowledge of actual temperature at the surgical site as well as the flow condition. Therefore, the surgeon has to balance between precautionary breaks for reducing thermal injury risk and the benefits of shorter operating time entirely based on their experiences.

On the other hand, in the current laser lithotripsy surgery, maintaining uninterrupted and adequate irrigation to the surgical site requires coordination of critical tasks by the surgeon and OR staff. The OR staff's manual tasks include constant visual monitoring of the irrigation fluid supply, manually increasing/adjusting pressure of the pressure cuff to maintain the pressure in feeding the irrigation fluid, replacing empty irrigation fluid bags without interruption of the laser lithotripsy procedure followed by reapplication of pressure cuff over the irrigation fluid bags and elevation of the irrigation fluid bags for gravity feeding, and timely verbal communication with the operating surgeon if irrigation fluid runs low or runs out. These tasks require the supporting staff's constant vigilance on irrigation fluid management. However, adequate fluid irrigation may be interrupted for multiple reasons, such as a drop of pressure in pressure cuff, the irrigation fluid bags running out while OR staff is distracted by other assigned duties, insufficient gravity feeding, or primary or secondary irrigation valves being shut off. A transient irrigation loss occurs during laser lithotripsy may not be known by operating surgeon, which would result in a prolonged heat transmission to the surgical site and inadvertently place the patient at risk of thermal injury and adverse outcomes.

The laser ablation surgery system of the present invention has overcome the deficiencies of the existing surgical laser system by providing effective safety measures at several levels. The safety measures of the present system encompass different stages of the surgical procedure. First, as described above, before the laser ablation begins, the risk calculator of the system control performs a preoperative risk assessment based on selected laser settings, etc. The preoperative risk assessment generates a preoperative safety guideline to the operating surgeon on safe laser deployment and management of irrigation fluid, such as recommending the maximum time of a continuous laser emission or frequency of pause of laser emission to prevent overheating, the duration of laser idle time to allow the irrigation fluid to cool down the surgical site between segments of laser emission, and a minimum flow rate of the irrigation fluid for dissipating heat at the surgical site, and a maximum fluid pressure at the surgical site to avoid fluid pressure injury risk. Therefore, before activating laser, the surgeon is alerted how to proceed with the procedure with specific intraoperative precautions. This preoperative safety feature is particularly beneficial in the situations when a new laser setting is used by a surgeon or a new laser is implemented, or when a surgeon does not have experience in a specific laser lithotripsy procedure.

Then, during the laser ablation surgery, the risk calculator actively monitors the temperature of the irrigation fluid at the surgical site detected by the temperature sensor in real time. The system control issues warnings or stop laser emission if the temperature of the irrigation fluid at the surgical site reaches a predetermined surgical site irrigation fluid temperature threshold during the procedure. Moreover, during the surgery, the flow control actively monitors the flow rate of the irrigation fluid detected by the flow sensor. The system control stops laser emission if the flow sensor detects the flow rate violates the predetermined irrigation flow criteria. Furthermore, during the surgery, the system control actively monitors the fluid pressure of the irrigation fluid at the surgical site as detected by the fluid pressure sensor. The system control stops laser emission if the fluid pressure sensor detects the fluid pressure violates the predetermined fluid pressure criteria.

These intraoperative monitoring and safety control features of the present system substantially reduce potential risks of thermal injuries and fluid pressure injuries and provide the operating surgeon and OR staff opportunities to take timely corrective actions to avoid adverse outcomes. This is a significant improvement in patient safety in comparison to the existing laser lithotripsy surgeries that only rely on the surgeon's judgement and staff's collaboration, where there is a lot of "what must go right" to ensure a safe operation.

In addition to intraoperative monitoring and safety control, the risk calculator further performs intraoperative thermal injury assessment and fluid pressure injury assessment. The risk calculator determines a degree of thermal injury risk, and a degree of fluid pressure risk, at the surgical site during the laser ablation surgery, for example, providing a qualifying thermal injury risk score, and optionally a qualifying fluid pressure injury risk score, to the surgeon during and at the conclusion of the surgery. The qualifying thermal injury risk score, and the qualifying fluid pressure injury risk score, associated with each surgery can be utilized by the surgeon intraoperatively or postoperatively.

During the surgery, for example, if a high thermal injury risk score is indicated by the system, the surgeon can timely take actions to mitigate further risks, such as shortening laser radiation time, increasing duration of the pause, or increasing flow rate of the irrigation fluid. Postoperatively, if a high thermal injury risk score is indicated by the system for the surgical procedure, the surgeon can make precautionary postoperative management decision, such as stent placement and interval imaging. Timely knowledge of a potential risk helps surgeons to prevent severe clinical complications, particularly when earlier postoperative symptoms are silent or mild. With timely intraoperative safety control and proactive postoperative management, morbid events, such as ureteral stricture, loss of renal function, bladder mucosal scald burn, and osteitis pubis, can be prevented. During a surgery, as another example, if a high fluid pressure injury risk score is indicated by the system, the surgeon can timely take actions to mitigate further risks, such as reducing inflow of the irrigation fluid to the surgical site, or increase the fluid outflow from the surgical site, or both.

As can be appreciated, the multi-level safety measures provided by the present system through the course of the surgical procedure fundamentally change safety practice in the field of laser ablation surgeries, particularly in ureteroscopic laser lithotripsy for treating urinary tract calculi where the surgical site tends to have a very limited space and thus the surrounding soft tissue is particularly prone to thermal injury. These comprehensive safety measures not only guide the operating surgeon through the surgical procedure, but also improve postoperative management and overall outcomes.

The real time temperature monitoring, and the real time fluid pressure monitoring, provided by the present system provides transparency and timely information on the conditions at the surgical site, which removes the blindness in current intraoperative temperature management and fluid pressure management, and eliminates the guessing game in laser deployment. The system substantially reduces the likelihood of human errors, such as potential judgement errors in laser deployment by the operating surgeon or technical errors or oversight in irrigation fluid management by the supporting staff. The safety measures of the present system relieve burdens from the operating surgeons and give them more confidence in laser safety. These measures reduce stress of working environment and allow surgeons to concentrate on the surgical procedure. This would ultimately reduce waste of time in temperature and irrigation managements in current laser surgery practice and improve operating room efficiency and cost.

The intraoperative thermal injury assessment and identifying the degree of thermal injury risk at the surgical site in real time during the laser ablation procedure, such as the qualifying thermal injury risk score provided by the risk calculator of the present system during the surgery, are unprecedented in laser ablation surgeries. It revolutionizes non-target tissue intraoperative monitoring and thermal injury risk management. The present system provides insight knowledge of non-target tissue at the surgical site which has never been available to the operating surgeon before. Providing the qualifying thermal injury risk score during an on-going procedure would alert the surgeon to take timely corrective actions, which could not happen previously without any indication from existing laser surgery systems. The qualifying thermal injury risk score provided by the present system informs the surgeon a potential thermal injury occurred during the surgery which would be unknown otherwise. The qualifying fluid pressure injury risk score provided by the present system informs the surgeon a potential fluid pressure injury occurred during the surgery which would be unknown otherwise. This would lead the surgeon to implement proactive postoperative measures to prevent severe adverse outcomes.

Moreover, as can be further appreciated that the real time data collected by the present system during laser ablation can also be used for clinical research for further improvement of surgical techniques, and can be used for further development of surgical laser technology for future products.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the scope of this invention as described in the above specification and defined in the appended claims and their legal equivalents.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted herein by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

Although specific embodiments of the subject matter have been disclosed, those having ordinary skill in the art will understand that changes can be made to the specific embodiments without departing from the scope of the disclosed subject matter. The scope of the disclosure is not to be restricted, therefore, to the specific embodiments, and it is intended that the appended claims cover any and all such applications, modifications, and embodiments within the scope of the present disclosure.

What is claimed is:

1. A laser ablation surgery system with safety control of surgical site temperature, the system comprising:
   (a) a laser source configured to produce a laser beam at a wavelength absorbable by an ablation target through a laser fiber connected thereto;
   (b) an endoscope having one or more lumens with at least one lumen configured to feed an irrigation fluid therethrough and having at least one temperature sensor disposed at a distal end of the endoscope, the temperature sensor being configured to monitor a temperature of the irrigation fluid at a surgical site of a laser ablation surgery in real time; and
   (c) a system control operably connected to the at least one temperature sensor, the system control comprising a processor communicatively coupled with an intraoperative surgical patient injury risk calculator that generates a patient injury risk score based on a patient injury calculation risk model that combines a plurality of weighted risk factors to generate the patient injury risk score, where each weighted risk factor includes a particular patient injury risk factor that has a value within a predetermined scale to indicate a level of patient injury risk associated with the particular patient injury risk factor and further includes a weight value which is applied to the particular patient injury risk factor according to an importance of the particular weighted risk factor to an overall calculation of the patient injury risk score, and wherein the intraoperative surgical patient injury risk calculator is configured to calculate a real time patient thermal injury risk score based on the patient injury calculation risk model which combines the plurality of the weighted risk factors to generate the real time patient thermal injury risk score, and wherein one of the weighted risk factors being associated with the temperature of the irrigation fluid at the surgical site detected by the at least one temperature sensor during the laser ablation surgery.

2. The system of claim 1, wherein the intraoperative surgical patient injury risk calculator comprises the patient injury calculation risk model including at least one predetermined surgical site irrigation fluid temperature injury risk threshold which the processor compares to the calculated real time patient thermal injury risk score to generate a real time patient thermal injury risk assessment.

3. The system of claim 2, wherein the real time thermal injury risk assessment identifies a degree of thermal injury risk, within a risk scale indicating probabilities of thermal injury, at the surgical site during the laser ablation surgery.

4. The system of claim 2, wherein the system control further comprises a laser control operably connected to the laser source, and the intraoperative surgical patient injury risk calculator is further configured to monitor the temperature of the irrigation fluid at the surgical site during the laser ablation surgery and the system control is configured to automatically activate the laser control when the intraoperative surgical patient injury risk calculator calculates a real time patient thermal injury risk score that reaches the at least one predetermined surgical site irrigation fluid temperature injury risk threshold.

5. The system of claim 4, wherein the at least one predetermined surgical site irrigation fluid temperature injury risk threshold is a critical surgical site irrigation fluid temperature injury risk threshold beyond which soft tissue at the surgical site sustains a thermal injury, and the system control is configured to activate the laser control to stop or reduce laser emission from the laser source when the intraoperative surgical patient injury risk calculator indicates the temperature of the irrigation fluid at the surgical site reaching the critical surgical site irrigation fluid temperature injury risk threshold.

6. The system of claim 1, wherein the at least one temperature sensor is disposed in one of the lumens, protruding about 1 to 4 mm from the distal end of the endoscope.

7. The system of claim 1, wherein the at least one temperature sensor is built in the distal end of the endoscope.

8. The system of claim 1, wherein the system control further comprises a laser control operably connected to the laser source, and wherein the system further comprises one or more irrigation flow sensors fluidly connected to the at least one lumen of the endoscope and operably connected to the system control, and the intraoperative surgical patient injury risk calculator further comprises at least one predetermined irrigation flow criteria, and wherein the system control is configured to activate the laser control when the intraoperative surgical patient injury risk calculator indicates a violation of the predetermined irrigation flow criteria.

9. The system of claim 8, wherein the predetermined irrigation flow criteria is associated with a minimum flow rate of the irrigation fluid while the laser beam is emitted, and the system control is configured to activate the laser control to stop or reduce laser emission from the laser source when the intraoperative surgical patient injury risk calculator indicates a flow rate of the irrigation fluid below the minimum flow rate.

10. The system of claim 8, wherein the system control further comprises a flow control configured to adjust a flow rate of the irrigation fluid when the intraoperative surgical patient injury risk calculator indicates a violation of the predetermined irrigation flow criteria or indicates the temperature of the irrigation fluid at the surgical site reaching at least one predetermined surgical site irrigation fluid temperature threshold.

11. The system of claim 10, wherein the system further comprises one or more pressure sensors fluidly connected to the irrigation fluid and operably connected to the system control, and the predetermined irrigation flow criteria is associated with an irrigation fluid pressure threshold, and the flow control is configured to adjust the flow rate of the irrigation fluid when the intraoperative surgical patient injury risk calculator indicates a pressure of the irrigation fluid at the surgical site reaching the irrigation fluid pressure threshold.

12. The system of claim 1, wherein the endoscope is an ureteroscope or a cystoscope, and the ablation target is one or more stones in kidney, ureter, bladder or urethra of a patient.

13. A laser ablation surgery system with safety control of surgical site temperature, the system comprising:
(a) a laser source configured to produce a laser beam at a wavelength absorbable by an ablation target through a laser fiber connected thereto;
(b) an endoscope having one or more lumens with at least one lumen configured to feed an irrigation fluid therethrough and having at least one temperature sensor disposed at a distal end of the endoscope, the temperature sensor being configured to monitor a temperature of the irrigation fluid at a surgical site of a laser ablation surgery in real time; and
(c) a system control operably connected to the at least one temperature sensor, the system control comprising a patient injury risk calculator configured to perform a real time thermal injury assessment utilizing the temperature of the irrigation fluid at the surgical site detected by the at least one temperature sensor during the laser ablation surgery; and
wherein the patient injury risk calculator is configured to further perform a preoperative thermal injury risk assessment and generate a preoperative thermal safety guideline for a selected laser ablation procedure.

14. The laser ablation surgery system of claim 13, wherein the patient injury risk calculator generates a patient injury risk score based on a patient injury calculation risk model that combines one or more weighted risk factors to generate the patient injury risk score, where each weighted risk factor includes a particular patient injury risk factor that has a value within a predetermined scale to indicate a level of patient injury risk associated with the particular patient injury risk factor and further includes a weight value which is applied to the particular patient injury risk factor according to an importance of the particular weighted risk factor to an overall calculation of the patient injury risk score, and wherein the patient injury risk calculator is configured to calculate a patient thermal injury risk score based on the patient injury calculation risk model which combines a plurality of the weighted risk factors to generate the patient thermal injury risk score, and wherein the preoperative thermal injury risk assessment and the preoperative thermal safety guideline for a selected laser ablation procedure are based on the patient thermal injury risk score.

15. A method of laser ablation surgery comprising:
(a) performing a laser ablation surgery on an ablation target using a laser ablation surgery system, said system comprising:
(i) a laser source configured to produce a laser beam at a wavelength absorbable by the ablation target through a laser fiber connected thereto;
(ii) an endoscope having one or more lumens with at least one lumen configured to feed an irrigation fluid therethrough and having at least one temperature sensor disposed at a distal end of the endoscope, the temperature sensor being configured to monitor a temperature of the irrigation fluid at a surgical site of a laser ablation surgery in real time; and
(iii) a system control operably connected to the at least one temperature sensor, the system control comprising an intraoperative surgical patient injury risk calculator that generates a patient injury risk score based on a patient injury calculation risk model that combines a plurality of weighted risk factors to generate the patient injury risk score, where each weighted risk factor includes a particular patient injury risk factor that has a value within a predetermined scale to indicate a level of patient injury risk associated with the particular patient injury risk factor and further includes a weight value which is applied to the particular patient injury risk factor according to an importance of the particular weighted risk factor to an overall calculation of the patient injury risk score, and wherein the intraoperative surgical patient injury risk calculator is configured to calculate a real time patient thermal injury risk score based on the patient injury calculation risk model which combines the plurality of the weighted risk factors to generate the real time patient thermal injury risk score, and wherein one of the weighted risk factors being associated with the temperature of the irrigation fluid at the surgical site detected by the at least one temperature sensor during the laser ablation surgery; and (b) monitoring the temperature of the irrigation fluid at the surgical site during the laser ablation surgery by the at least one temperature sensor, wherein the intraoperative surgical patient injury risk calculator calculates the real time patient thermal injury risk score based on the temperature of the irrigation fluid at the surgical site detected by the at least one temperature sensor during the laser ablation surgery.

16. The method of claim 15, wherein the intraoperative surgical patient injury risk calculator comprises the patient injury calculation risk model including at least one predetermined surgical site irrigation fluid temperature threshold which the intraoperative surgical patient injury risk calculator uses to evaluate the calculated patient thermal injury risk score to generate a real time patient thermal injury risk assessment.

17. The method of claim 15, wherein the system further comprises one or more irrigation flow sensors fluidly connected to the at least one lumen of the endoscope and operably connected to the system control, and the intraoperative surgical patient injury risk calculator further comprises a weighted risk factor associated with irrigation flow rate and wherein the method further comprises activating a laser control when the intraoperative surgical patient injury risk calculator indicates a violation of a predetermined irrigation flow criteria.

18. The method of claim 15, wherein the laser ablation surgery is a laser lithotripsy, and the ablation target is one or more stones in kidney, ureter, bladder or urethra of a patient.

* * * * *